(12) United States Patent
Theodoracopulos et al.

(10) Patent No.: US 6,964,638 B2
(45) Date of Patent: *Nov. 15, 2005

(54) MEASURING COGNITIVE IMPAIRMENT

(75) Inventors: Alexis Theodoracopulos, New York, NY (US); Darin Kaplan, New York, NY (US); Vladislav Shchogolev, Brooklyn, NY (US); David M. Erlanger, New York, NY (US); Philip Yee, New York, NY (US); McDonald Comrie, Staten Island, NY (US)

(73) Assignee: Pan Medix, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/239,383

(22) PCT Filed: Jan. 23, 2001

(86) PCT No.: PCT/US01/02189

§ 371 (c)(1),
(2), (4) Date: Sep. 20, 2002

(87) PCT Pub. No.: WO01/72217

PCT Pub. Date: Oct. 4, 2001

(65) Prior Publication Data

US 2003/0073885 A1 Apr. 17, 2003

Related U.S. Application Data

(63) Continuation-in-part of application No. 09/494,475, filed on Jan. 31, 2000.

(51) Int. Cl.[7] .................................................. A61B 5/00

(52) U.S. Cl. ........................................ 600/300; 128/920

(58) Field of Search ................................ 600/300–301; 128/897, 920, 904; 434/236–238, 258, 322–323, 335, 362

(56) References Cited

U.S. PATENT DOCUMENTS 5,913,310 A 6/1999 Brown
6,280,198 B1 * 8/2001 Calhoun et al. ............ 434/236

OTHER PUBLICATIONS http://www.parrotsoftware.com (Parrot Software publ., Aug. 8, 2000).
http://www.maddak.com/hptherap/hpspec/loc16.htm (Maddak Inc. publ., Aug. 8, 2000).
http://www.unlv.edu/colleges/Education/EP/n1test_2.htm (Univ. of Nevada at Las Vegas publ., Aug. 8, 2000).
The Catalog for Psychological Assessment (The Psychological Corporation publ., 2000).
Information Disclosure Statement for U.S. Appl. No. 09/494,475, (issue fee paid but patent not yet issued) (PanMedix Inc., Aug. 9, 2000).
David M. Erlanger at al., "Neuropsychology of Sports–Related Head Injury," 13 Clin. Neuropsychol. 193 (1999).
Robert C. Cantu, "Head Injuries in Sport".
David Maddocks et al., "Neuropsychological Deficits Following Concussion," 10 Brain Injury 99 (1996).
Kenneth C. Kutner et al., "Computerized Neuropsychological Assessment in the NFL," Sports Science Symposium (NFL Physician Soc., Feb. 7, 1997).
Anton D. Hinton–Bayre, "Mild Head Injury and Speed of Information Processing," 19 J. Clin. Exp. Neuropsychol. 275 (1997).
Mark R. Lovell et al., "Neuropsychol. Assment of the College Football Player," 13 J. Head Trauma Rehabil. 9 (1998).

(Continued)

*Primary Examiner*—Max F. Hindenburg
*Assistant Examiner*—Michael Astorino

(57) ABSTRACT

System (s100, s200, s300, s400) to quantify cognitive performance.

38 Claims, 5 Drawing Sheets

OTHER PUBLICATIONS

Figure 1:
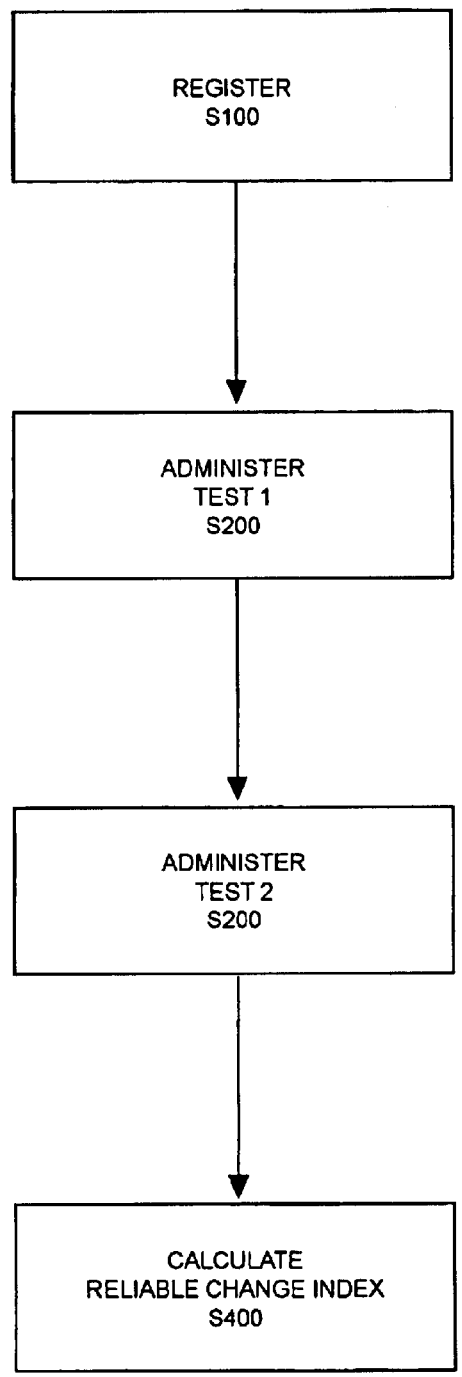
Figure 2:
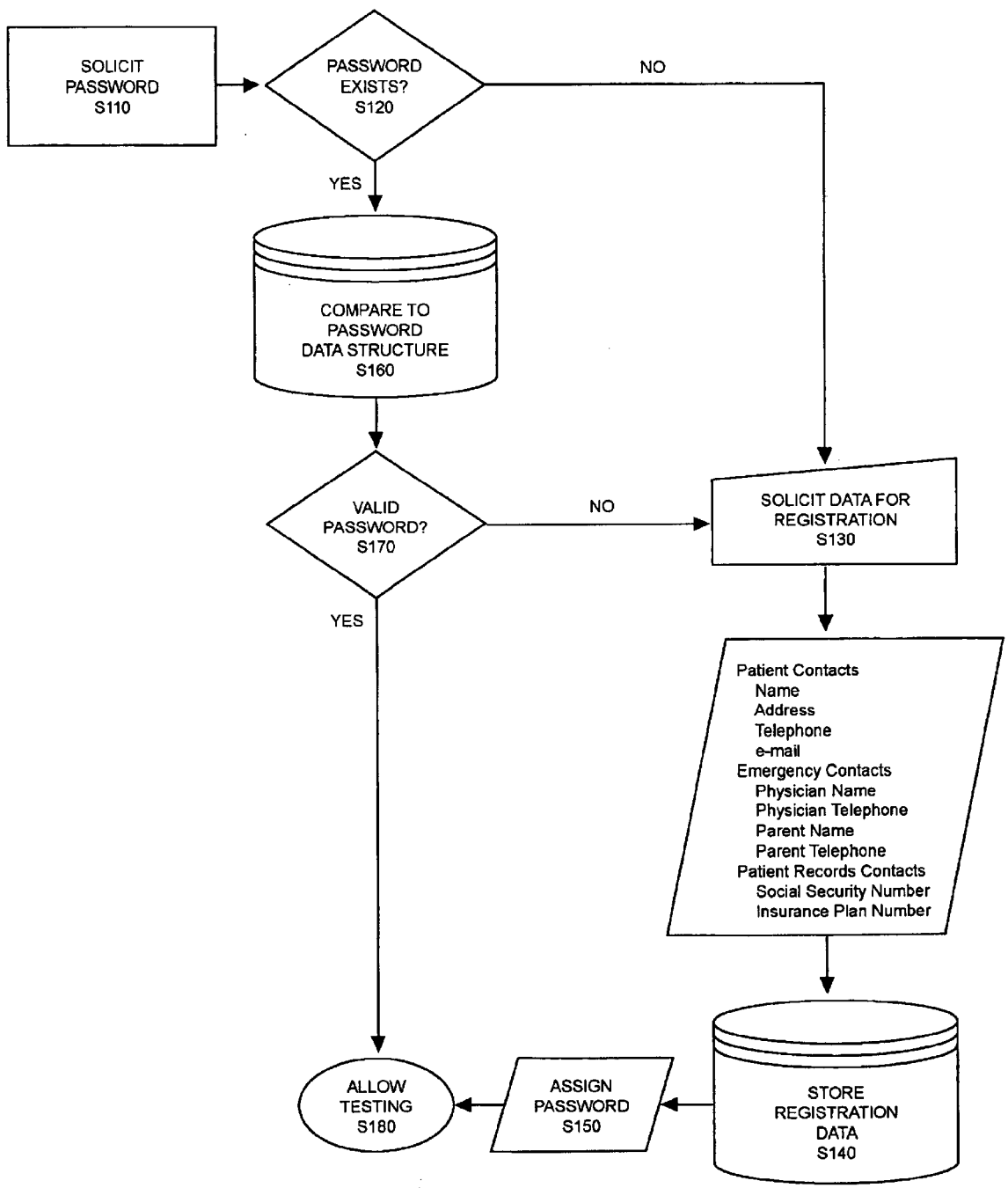
Figure 3:
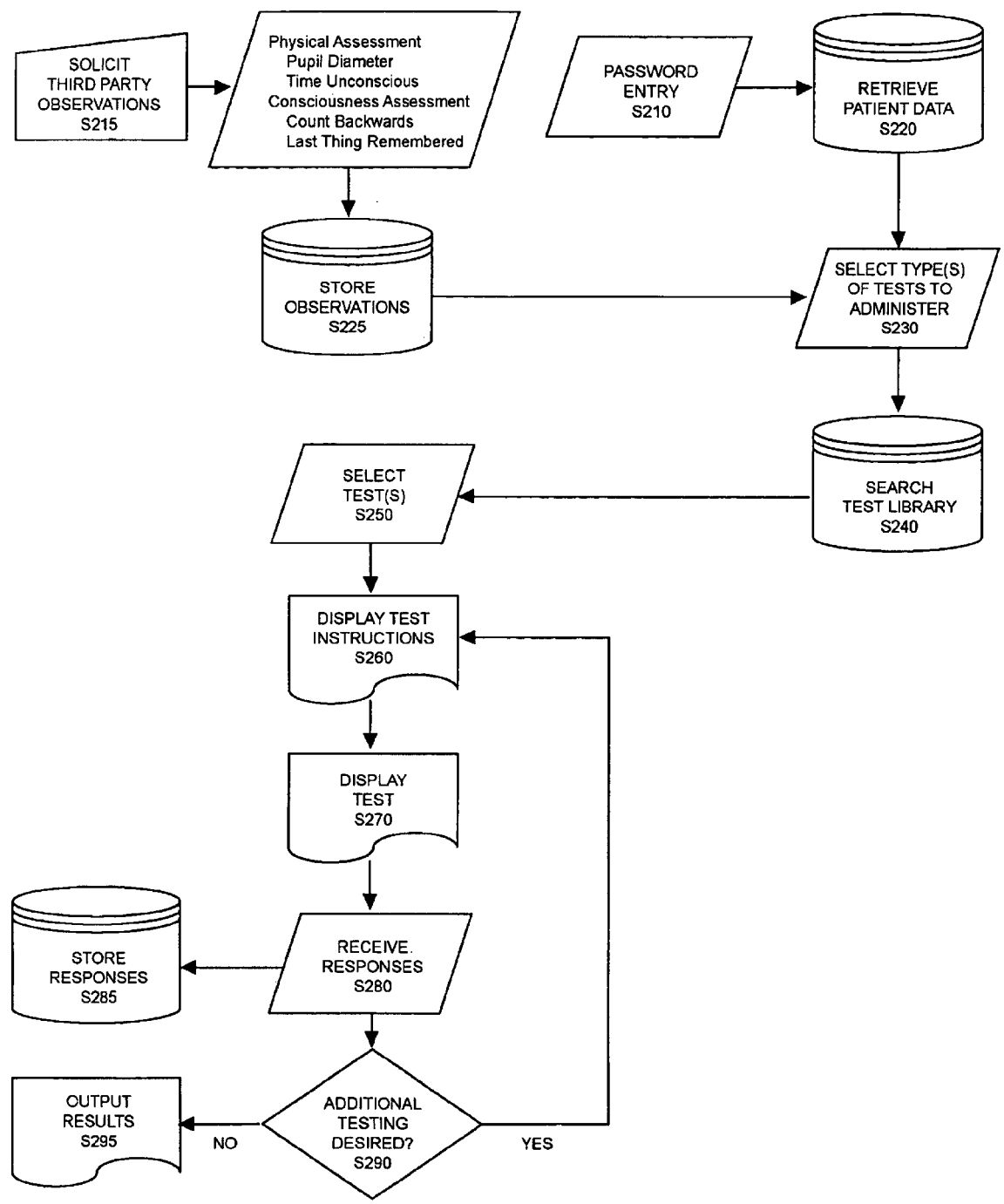
Figure 4:
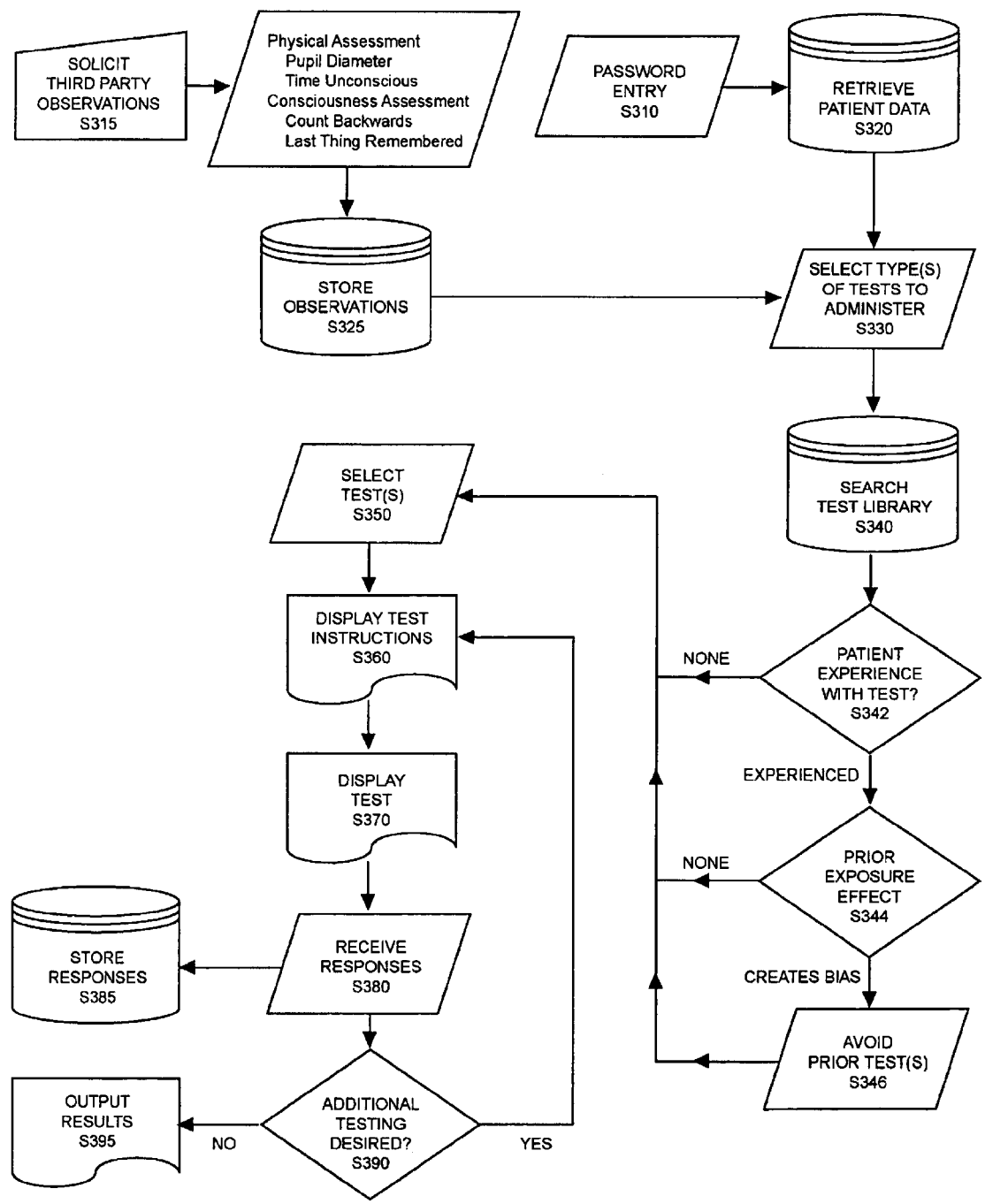
Figure 5:
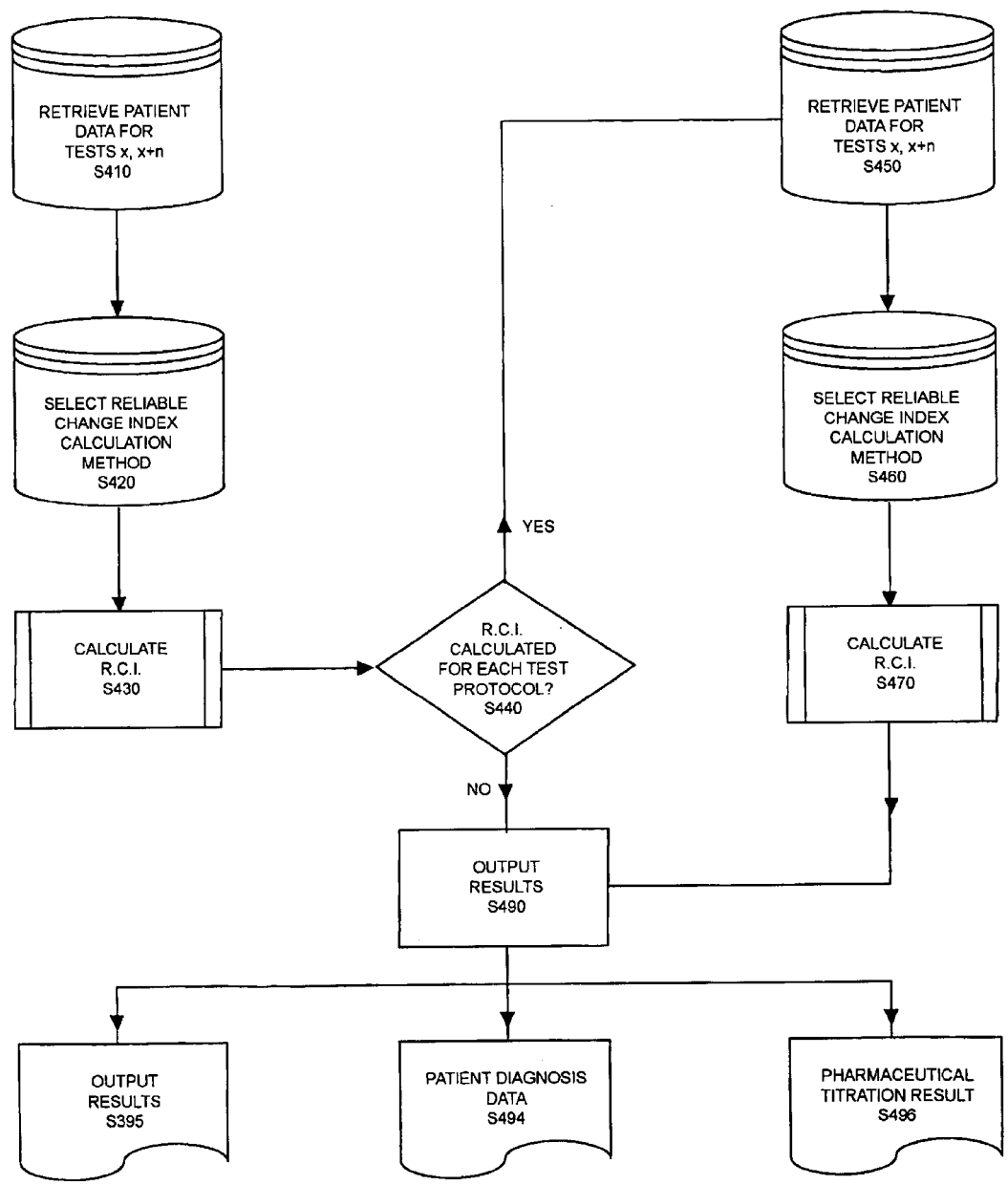

Joseh Bleiberg et al., "Future Directions for the Neuropsychological Assment of Sports Concussion," 13 J. Head Trauma Rehabil. 36 (1998).
Nancy R. Temkin et al., "Detecting Significant Change In Neuropsychological Test Performance," 5 J. Int'l Neuropsychol. Soc. 357 (1999).
Anton D. Hinton–Bayre et al., "Concussion in Contact Sports," 21 J. Clin. Exper. Neuropsychol. 70 (1999).
Robert K. Heaton et al., "Detecting Change," 16 Arch. Clin. Neuropsychol. 75 (2000).
Stephen N. Macciocchi et al., "The Impact of Mild Head Injury Frequency On Neuropsychological Functioning."
Michael Collins et al., "Current Issues in Managing Sports-Related Concussion," 282 JAMA 2283 (1999).
Michael Collins et al., "Relationship Between Concussion and Neuropsychological Performance," 282 JAMA 964 (1999).
Erik J.T. Matser et al., "Neuropsychological Impairment In Amateur Soccer Players," 282 JAMA 971 (1999).
M. Mrazik et al., "Neuropsychological Assessment of College Football Players."
Joseph Bleiberg et al., "Factor Analysis Of Computerized and Traditional Tests," 14 Clin. Neuropsychol. 295 (2000).
Ruben J. Echemendia et al., "Neuropsychological Evaluation of Mild Traumatic Brain Injury In Sports," Course No. 42 (Nat. Acad. Neuropsychol., publ).
Ruben J. Echemendia et al., "Mild Traumatic Brain Injury In Sports: Neuropsychology's Contribution To A Developing Field."
David M. Erlanger et al., "Neuropsychological Test Performance Prior To and Following Sports Related Mild Traumatic Brain Injury."
Trademark registration for Federal trademark "T.O.V.A." (Apr. 13, 2002) (Reg. No. 1,713,349) (showing alleged date of first use in commerce of Jan. 4, 1990).
Othmer, Susan F. et al., "Evaluation and Remediation of Attentional Deficits," (Dec. 1992).
Attention Technology, Inc., "If you Are Interested in ADD / ADHD Then You Should Be Interested In T.O.V.A." (published as world–side web page) (Apr. 2002).
Universal Attention Disorders, Inc., "Annnotated Bibliography for the T.O.V.A.," (1997).
Bailie, R. et al., "Effects of Temazepam Premedication on Cognitive Recovery Following Alfentanil–Propofol Anaesthesia," 63 Brit. J. Anaesth. 68 (1989).
Sahakian, B.J. et al., "Further Analysis of the Cognitive Effects of Tetrahydroaminoacridine (THA) in Alzheimer's Disease," 110 Psychopharmacol. 395 (1993).
Elliott, R., "Effects of Methylphenidate on Spatial Working Memory . . . ," 131 Psychopharmacol. 196 (1997).
Greenberg, L.M., "An Objective Measure of Methylphenidate Response: Clinical Use of the MCA," 23 Psychopharmacol. Bull. 279 (1987).
Comptronic Devices Ltd., "T.O.V.A. and T.O.V.A.–A.; the state of the art visual and auditory continuous performance tests . . . ," (product brochure) (undated).
Leark, R.A. et al., "T.O.V.A. Professional Manual" pp. i–iv, 18–23, 64–94 (Universal Attention Disorders, Inc. 1996).
Greenberg, L.M. et al., "T.O.V.A. Clinical Guide" pp. i–iiii, 1, 7–11, 20–25, 72–78 (Universal Attention Disorders, Inc. 1996).
Rudy, T.E., "Differential Treatment Responses of TMD Patients as a Function of Psychological Characteristics," 61 Pain 103 (1995).

* cited by examiner

MEASURING COGNITIVE IMPAIRMENT

This application is a 371 of PCT/US01/02189 filed Jan. 23, 2001, which is a continuation-in-part of Ser. No. 09/534,545 filed on Mar. 27, 2000 now abandoned, which is a continuation-in-part of application Ser. No. 09/454475, filed on Jan. 31, 2000.

BACKGROUND

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Cognitive function can be impaired by physical insults such as radiation or chemical exposure. Measuring changes in cognitive function is thus an important way to quantify the adverse cognitive effects of such insults.

Intentional exposure to electro-magnetic radiation (including electricity) may cause cognitive impairment. For example, electro-convulsive therapy, used in psychiatric treatments, is acknowledged in the art to be beneficial to certain patients. It is, however, difficult to quantify how beneficial it is, as the cognitive impairment effects of ECT are difficult to measure. Similarly, radiation therapy (as, for example, for a cancer patient) is acknowledged to create memory loss. It is, however, difficult to measure this memory loss. Other electromagnetic exposure, such as exposure to laser light, or even excess exposure to sunlight, may impair cognition.

Similarly, accidental exposure to radiation may impair cognition. For example, it has been argued that cellular telephones, by exposing the user's brain to electromagnetic radiation, can impair cognition. The accuracy of this fear is, however, difficult to measure.

Other types of physical intervention or therapy may affect cognition. For example, vaccines, gene therapy and other kinds of biological implants (e.g., transplants, stem cell implants and fetal cell implants), exposure to toxins, molds or chemicals in the environment (including, for example, Gulf War syndrome and other exposure to pollution or weapons chemical, nuclear, conventional or biological), ingestion of vitamins, herbs, over the counter compositions or homeopathic preparations or other ingested things, may impair cognitive function, but measuring such effects until now has been prohibitively difficult.

There has thus been a need for a way to measure cognitive function more precisely, to quantify changes in cognitive function.

Published patents include the following:

Steven J. Brown discloses a method for diagnosis and treatment of psychological and emotional disorders using a microprocessor based video game, U.S. Pat. No. 5,913,310. Disclosed examples include "schizophrenia, depression, hyperactivity, phobias, panic attacks, anxiety, overeating, and other psychological disorders" such as "personality disorders, obsessive-compulsive disorders, hysteria, and paranoia."

Joel S. Douglas et al. discloses an analyte testing system with test strips, U.S. Pat. No. 5,872,713. These test strips are effective to assay for certain chemical changes in a patient, but have not been used to assay cognitive dysfunction or impairment.

Patrick Lichter discloses a personal computer card for collecting biological data, U.S. Pat. No. 5,827,179. The patent claims a portable computer card used with an air pressure transducer, see id. at claim 1, or a "biological data receiver," see id. at claim 6. The biological data receiver "can be adapted to receive biological data from a pulse oximetry sensor" or "from an ECG sensor." This system may be effective to assay for certain physical changes in a patient such as pulmonary function, but it has not been used to assay cognitive dysfunction or impairment.

Tom Marlin discloses a system for constructing formulae for processing medical data, U.S. Pat. No. 5,715,451. The patent says that rather than providing a prepared statistical analysis package, Marlin discloses a computer interface to construct statistical and other mathematical formulae to ease the analysis of clinical data.

Stephen Raymond et al. discloses a health monitoring system that "tracks the state of health of a patient and compiles a chronological health history . . . us[ing] a multiparametric monitor which . . . automatically measures and records a plurality of physiological data from sensors in contact with the patient's body," wherein "[t]he data collected is not specifically related to a particular medical condition" such as cognitive dysfunction. U.S. Pat. No. 5,778,882.

William Reber et al. discloses a medical communication timing system comprising an output device that generates an alert for the proper time to take a first medicine and a second medicine. U.S. Pat. No. 5,950,632 and U.S. Pat. No. 5,950,632.

Michael Swenson et al. discloses a virtual medical instrument for performing medical diagnostic testing, U.S. Pat. No. 5,623,925 and U.S. Pat. No. 5,776,057. The instrument "includes a universal interface having a number of electrical contacts and sets of electrical conduits associated with the different stored diagnostic test protocols. * * * The system is constructed to enable the selected diagnostic teat protocol to be performed on a patient after the corresponding set of electrical conduits are connected to the Universal interface contacts and to the patient."

Paul Tamburini et al. discloses a diagnostic assay for Alzheimer's disease based on the proteolysis of the amyloid precursor protein, U.S. Pat. No. 5,981,208.

Not disclosed in the art—nor even suggested in it—is our non-invasive, computerized invention to accurately measure cognitive function and changes in cognitive function over time. There is a need for such an invention that is easy to administer, rapid, less expensive, and accurate enough to enable assessment of the cognitive impairment impact of a wide variety of agents or environments.

SUMMARY

We have invented a solution that enables one to better assess the cognitive impairment impact of various physical insults. Our solution works at minimal cost per administration, compared to a roughly 55% to 65% accuracy and approximately $2,000 cost per assay for the personally administered assays previously known in the art.

Further, our assay shows consistent results regardless of the identity or experience level of the treating physician. Thus, the results obtained from our test can be pooled and compared among patients located in different study locations, with a level of data comparability and accuracy not before available in the art. This data comparability greatly improves the usefulness and informative ness of the test responses. It improves the accuracy of the diagnosis of cognitive impairment in an individual patient. It enables clinical research done at different locations, and by different health care practitioners, to be easily compared. It improves the ability of research scientists to correctly evaluate the cognitive impact of a potential neurotoxin.

DETAILED DESCRIPTION

Our invention entails using a computer to show a patient a series of cognitive dysfunction tests, receiving the patient's test responses, and analyzing these responses to assess cognitive dysfunction in the patient, whereby a conclusion regarding whether symptoms of cognitive dysfunction probably exist or are absent in the patient. Saliently, in contrast to the prior art, which teaches manual, one-time testing, our invention enables the comparison of multiple test results over time, to assess the change over time in a patient's responses. The patient's degree and rate of change over time is, in certain ways, significantly more informative that a static, one-time score.

The term "cognitive dysfunction testing protocol" connotes cognitive testing protocols to measure cognitive function (immediate and short-term memory and pattern recognition, for example) by providing the patient or user with a series of sensory stimuli, and measuring the user's ability to consciously and voluntarily respond to and remember said stimuli. To make our invention, one can use any of a wide variety of cognitive function testing protocols. Examples known in the art include the series of tests commercially available from The Psychological Corporation, a division of Harcourt Brace Jovanovich Publishers, New York, N.Y. The precise identity of the testing protocols is not important.

In our preferred embodiment, the cognitive dysfunction testing protocols are visual or auditory. That is to say, they entail showing the user a series of images or sounds and measuring the user's ability to remember and respond to these. We disclose and discuss below the specific details of some examples of cognitive dysfunction testing protocol.

Our invention is not, however, limited to these specific testing protocols disclosed below. One can readily make our invention using other visual testing protocols. One can even make versions of our invention using other types of sensory response protocols. For example, one can make our invention using auditory stimuli, in place of visual stimuli. This may be necessary for assaying blind or visually-impaired users. This may also be preferred as advantageous to garner a more full picture of the patient's audio, visual, and even tactile responsiveness to cognitive testing protocols.

As used herein, the term "Memory" denotes computer-readable memory on tangible media, able to store the test protocols, receive user responses, store a response evaluation protocol, and process said user responses according to said response evaluation protocol to generate a result (or "score"). In one version of our invention, the Memory is one single piece of electronic hardware, able to perform all of the required functions.

The Memory need not be one physical unit, however. In one preferred version, the Memory which receives the patient's responses into Memory which is physically located in an Internet-capable wireless phone, while the Memory which stores the most up-to-date version of the cognitive dysfunction testing protocol, and the software to perform the complex user response evaluation, is in Memory physically located in an Internet accessible computer server. One of the advantages of our invention is that one can make it using an extremely wide variety of physical Memory configurations, as long as one provides Memory to perform each of the required functions.

As used herein, the term "computing apparatus" includes personal computer microprocessors for both stand alone computers and those connectable to an external network or software source such as the Internet. The term also includes any electronic hardware which can execute the neurological testing routine herein described.

Thus, for example, our invention can be made using a personal handheld electronic organizer, such as the PALM PILOT (TM), commercially available from Palm Computing, Inc., Santa Clara, Calif. a WINDOWS CE (TM) (Microsoft Corporation, Redmond, Wash.) or wireless application protocol standard or blue tooth standard appliance, a wireless telephone with adequate memory, a wireless communications device connectable to an external software source (such as the Internet), or a dedicated medical device whose sole function is to execute the cognitive testing protocols. Our invention can even be made using a television set, where the television is capable of receiving test responses from the subject, via a television remote-control device, for example. This is one of the advantages of our invention—it is extraordinarily flexible, and can be easily produced in an extremely wide variety of hardware. Our invention thus can be made in various versions which are durable, portable, inexpensive, etc . . . , as desired by a given kind of user.

As used herein, the term "Display" denotes apparatus to render the testing protocol perceivable by the user. In our preferred version, the display is the visual display screen on a portable personal computer (or PDA device) or on a wireless telephone. One can use other visual displays, however, including television screens or projector-based systems such as one finds for visual acuity testing at the optometrist's. Further, where one uses non-visual testing protocols, the Display will necessarily entail the ability to display the non-visual information For example, if one uses sound auditory testing protocols, then the Display will need to include audio speakers or the like.

As used herein, the term "Response Input" denotes apparatus that the test user can use to input their responses to the test protocol into the Memory. In our preferred version, the Response Input is a keyboard or personal computer "mouse." However, one can use a stylus for a hand-held computing device, punch pads or a joystick, and so forth, or other types of electronic devices (e.g., wireless telephones, handheld computing devices, touch screen displays) and non-keyboard devices as appropriate. For example, one can use a television infrared remote-control unit, where the Display is a television. The Response Input can be anything able to communicate the user's responses to the Memory.

As used herein, the term "user response analysis software" is software capable of analyzing the user's responses to the cognitive dysfunction testing protocol, to assess whether symptoms of cognitive dysfunction likely exist or are absent in the user, based on the user's responses to the cognitive dysfunction testing protocol. The user response analysis software includes a computer readable data structure on computer readable, tangible media to store both patient responses, and the statistical analysis protocols that use the patient's responses as variable inputs. Such statistical analysis allows the most information to be obtained from these responses. Used appropriately, the statistical analysis enables the user to draw more sensitive, sophisticated conclusions from the user's responses. Statistical analysis capability had not before been combined in a single system with cognitive-function data (response) gathering capability, before the immediate invention. We disclose in detail below our preferred version of user response analysis software.

The term "Output" denotes a device capable of outputting the results of the user response analysis software. In our preferred embodiment, the Output includes two components: (a) a computer display screen, the same screen used as the "Display" to display the tests to the patient; and (b) a communications device to communicate the user's test results from the user response analysis software to a Memory for storage and later retrieval. Alternatively, one may use a printer, a modem (including a wireless communication device), a disk drive, or any other combination of hardware appropriate for the given version of our invention. For example, with a blind user, the Output may be an audio speaker.

The term "communication network" includes communication networks both open (such as a ground-line telephone, a radio, or a broadcast television network or the Internet) and closed (such as an intranet or a restricted access wide area network or local area network).

As mentioned above, our invention is useful specifically to assess the effect on cognitive function of exposure to electromagnetic radiation, including accidental and intentional exposure. This includes nuclear medicine, excessive exposure to radiation including electric shock, sunlight, burns, heat stroke or heat exhaustion, and excess exposure to cold (frost-nip, frostbite, hypothermia, exposure, immersion, chilblains, pernio, etc . . . ).

One advantage of our invention, however, is that its application is not limited to any certain class of insult; rather, our invention can be used to inexpensively, easily and accurately assess the impact on cognitive dysfunction of any kind of physical insult. Thus, for example, our invention can be used to quantify the amount or cognitive impairment due to motion sickness, near drowning, decompression sickness (Caisson Disease and gas embolism), high-altitude sickness (acute mountain sickness, high altitude pulmonary edema, high altitude cerebral edema, Soroche, Puna, maroe, etc . . . ) any kind of non-drug medical therapy, such as ultra-sound treatment, electro-convulsion therapy, radiation therapy, and tissue transplants.

In addition to quantifying the cognitive effects of physical insult, our invention is useful to quantify the cognitive effect of illness and other physical conditions.

The best mode we currently know of also includes using our invention to evaluate the cognitive dysfunction impact (or side effect) of exposure to other physical insults, such as ambient radiation, cellular telephone radiation, or solar radiation.

Cognitive Dysfunction Testing Protocols

A version of our invention particularly effective for evaluating cognitive effects entails doing a patient assessment at least once before the stimulus (e.g., exposure to the radiation), and at least once after exposure. This version entails having the patient take a series of cognitive dysfunction tests before the patient has been exposed, and receiving the patient's test responses, and analyzing these responses, to form a "baseline" performance level for the patient, and to also—after the patient has been exposed—to have the patient take a series of cognitive dysfunction tests, and to receive the patient's test responses, and analyze these responses to form a new performance level for the patient, and to compare these new responses to the patient's earlier ("baseline") responses to then form a conclusion regarding whether symptoms of probable cognitive dysfunction exist.

In another version of our invention, the "baseline" is a composite of test results obtained by other, presumptively healthy people. Alternatively, the patient's insult-influenced results can be compared both to a standard "baseline," and to the patient's personal results in the absence of the insult.

In the best mode we currently know of to practice our invention, one uses cognitive dysfunction testing protocols such as the following ones. These specific protocols are protected by copyright, ©2000 Head Minder, Inc. and ©2000 Panmedix, Inc.

Administration of the testing protocols is preceded by displaying an ethical statement on the privacy of the test results and a legal disclaimer. The testing protocols begin only after the user's identity is verified by a test administrator, or by the user entering a code such as their social security number and a secret password. Before commencing the testing protocols, the user is informed that they should not take the tests if the user has recently used alcohol or other drugs capable of affecting cognitive ability.

Administration of the testing protocols is also preceded by gathering certain general information on the user. This information can be useful or necessary to best administer the tests and interpret the test results. This general information includes the patient's Name, the e-mail and street addresses and telephone numbers for the patient, the patient's physician, the local hospital, and the patient's legal guardian (if applicable), so that any of these can be contacted quickly in an emergency. In our preferred embodiment, the apparatus has a communications device such as wireless telephone capability or a modem. Similarly, we prefer to include contact information for the patient's health insurance provider, so that test information and results can be directly communicated to the insurer without intervening manual transcription. The patient's date of birth is, in our preferred embodiment, entered into the software and used to determine which version of certain testing protocols to administer (we prefer to provide certain testing protocols in several different versions, each version suitable for a certain age group). The Test Date can be entered automatically by the computing device if it has a timer/clock function. The patient's gender, sports played, dominant hand (right, left, ambidextrous, and known prior history of type and date of prior seizures, concussions, reading problems, special education classes, native language, etc . . . , all can be used to adjust or interpret the testing protocol results. A chart of pupil sizes can be included, to allow the patient (or someone else) to quantify the patient's pupil size(s).

The identity and regime for the physical insult (e.g., electro-convulsive therapy, or radiation therapy) in questions can optionally be entered. This enables one to integrate with the result analysis software, a function to advise on the suggested future regime for the insult.

If the testing protocol is supervised by someone other than the patient, we prefer to include an electronic "signature" to be entered by the test supervisor, to create a medical record authenticating who supervised the test.

We prefer that the testing protocols themselves be arranged or ordered to put at the very beginning those tests most indicative of the most severe cognitive impairment. This enables the software to rapidly triage patients and indicate, for patients with cognitive impairment which is severe, that medical intervention may be required immediately, without forcing the patient to complete each and every one of the testing protocols. Similarly, we prefer to order the testing protocols so that patients with superior cognitive function can, if desired, take a longer battery of assays, and obtain a statistically more accurate and precise measure of cognitive function.

At the beginning of the testing protocols, the user is shown the keyboard layout, and shown which keys are needed for responding. For each testing protocol, Screen Instructions are displayed on the Display, and the user must respond appropriately before the protocol begins.

Each cognitive function testing protocol comprises a series of stimuli shown to the user, to which the user must respond. While it is possible to make testing protocols which use words, we prefer to use protocols which are based on images, not words. This minimizes the data bias based on less than perfect literacy, using a nonnative language for the testing protocols, and the like.

Examples of cognitive function testing protocols include the following visual testing protocols:
Tracking Part I;
Tracking Part II
Incidental Learning Part I;
Incidental Learning Part II;
Matching;
Response Direction Part I;
Response Direction Part II;
Response Inhibition;
Memory Cabinet Learning;
Memory Cabinet Delayed Recall;
Scanning Speed and Accuracy;
Reaction Time;
Cued Reaction Time;
Visual Memory Part I;
Number sequencing;
Visual Memory Part II; and
Number recall.

These protocols are examples. Our preferred embodiment uses many different specific test protocols. This makes it less likely that a user will memorize a specific test protocol and the perceived "correct" responses to it.

We now more fully describe each these examples of testing protocols.

Tracking Part T Testing Protocol

At the beginning of this testing protocol, the Display displays the following Screen Instructions:

You are about to see a grid with 9 spaces, just like a tic-tac-toe board. A ball will appear in one of the nine spaces. A moment later, the ball will disappear. The ball will then reappear. If the ball appears in a different space, then do nothing. If the ball re-appears in the same space as the immediately preceding time, then press the SPACE BAR.

Press the SPACE BAR when you are ready to begin.

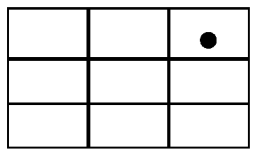

The ball is displayed in a square for 1,500 milliseconds, followed by 500 milliseconds of all blank squares. If the ball appears in the same square two times in a row, the patient should press the space bar. The patient inputs their responses into the Response Input, and thus into the Memory, for further processing by the patient response analysis software. We prefer the testing protocol to present approximately thirty stimuli over about one minute.

Tracking Part II Testing Protocol

At the beginning of this testing protocol, the Display displays the following Screen Instructions:

You are about to see the same grid as before. This time, press the SPACE BAR if the ball appears not in the space immediately preceding, but the space before that one.

The ball is displayed in the square for 1,500 milliseconds, followed by 500 milliseconds of blank squares. If the ball appears in the same square as the time before the previous time, the user should press the space bar. We prefer to display about sixty stimuli over about two minutes. The patient inputs their responses into the Response Input, and thus into the Memory, for further processing by the patient response analysis software. This test may be modified for patients with high cognitive functioning to require a response for the third preceding position, rather than the second or the immediately preceding one.

Incidental Learning Part I

At the beginning of this testing protocol, the Display displays the following Screen Instructions:

Soon you will see a series of pictures appear on the screen. Whenever you see a picture of a plant (such as a fruit, tree or vegetable), press the space bar. If you see a picture of anything else, then do nothing. Try to be fast without making mistakes. You are being timed on how fast you respond.

Press the space bar when you are ready to begin.

The Display then displays pictures of plants, animals, and everyday objects. Each picture is displayed for 2 seconds, followed by 1 seconds of blank screen. The patient inputs their responses into the Response Input, and thus into the Memory, or further processing by the patient response analysis software. We prefer to display about forty stimuli (about ten plants, 15 animals and 15 inanimate objects) over about two minutes.

Incidental Learning Part II

At the beginning of this testing protocol, the Display displays the following Screen Instructions:

Soon, you will see a series of pictures. Some are from the series you saw a few minutes ago, while some are new. When you see a picture that you recognize from a few moments ago, press the space bar. If you see a picture that you have not seen before, then do nothing. Try to be fast without making mistakes. You are being timed on how fast you are. Press the space bar when you are ready to begin.

The Display then displays pictures of plants, animals and everyday objects. About twenty images from the Incidental Learning Part I are repeated. Each picture is displayed for 2.0 seconds, followed by 1.0 second of blank screen. The patient inputs their responses into the Response Input, and thus into the Memory, for further processing by the patient response analysis software.

In our preferred embodiment, separate statistics for animate and inanimate picture responses are collected and compared. We prefer about forty stimuli over about two minutes. We prefer to give this test after Incidental Learning Part I and another, intervening task.

Matching

At the beginning of this testing protocol, the Display displays the following Screen Instructions:

You are about to see, for ten seconds, ten matching pairs of shapes laid out in a grid. Study the shapes' locations. The shapes will then be hidden under small squares. Once the shapes are hidden, use your mouse to click on any square. The shape hidden beneath the square will appear. Then, use your mouse to click on the square that you think covers the matching shape. If you do not find the matching shape, then both shapes will be covered again. Repeat the process until you find all the matching pairs. Try to make all the matches in as few tries as possible. You will not be timed. Press the space bar when you are ready to begin.

The user must find ten matching pairs of shapes. All pairs are initially displayed for ten seconds, and then covered. In the example above, the Display displays one shapes. The user must then try to find the location of the other. The patient inputs their responses into the Response Input, and thus into the Memory, for further processing by the patient response analysis software. If the user is correct, both shapes in the pair stay uncovered. Otherwise, both will be covered up again. The test continues until all matches are made or until the user attempts forty guesses. There is no time limit.

Response Direction Part I

At the beginning of this testing protocol, the Display displays the following Screen Instructions:

Soon, you will see numbers appear briefly on the screen. Place your left index finger on the 1 key and your right index finger on the 0 key. When you see the number "1" displayed on your screen, press number 1 on your keyboard. When you see the number "0" displayed on your screen, press number 0 on your keyboard. If you see any other number, do nothing. Try to be fast without making mistakes. You are being timed on how fast you respond. Press the spacebar when you are ready to begin.

The Display then displays a number for about 0.5 seconds, followed by 1.5 seconds of blank screen. The patient inputs their responses into the Response Input, and thus into the Memory, for further processing by the patient response analysis software. Responses can occur anytime before the next digit is displayed. We prefer displaying about sixty stimuli over about two minutes.

Response Direction Part II

At the beginning of this testing protocol, the Display displays the following Screen Instructions:

Soon, you will see numbers appear briefly on the screen. Place your left index finger on the 1 key and your right index finger on the 0 key. Do the inverse of what you did on the last test. That is, when you see the number "1" displayed on your screen, press number 0 on your keyboard. When you see the number "0" displayed on your screen, press number 1 on your keyboard. If you see any other number, do nothing. Try to be fast without making mistakes. You are being timed on how fast you respond. Press the spacebar when you are ready to begin.

The Display then displays a number for about 0.5 seconds, followed by 1.5 seconds of blank screen. Responses can occur anytime before the next digit is displayed. The patient inputs their responses into the Response Input, and thus into the Memory, for further processing by the patient response analysis software. We prefer displaying about sixty stimuli over about two minutes.

Response Inhibition

At the beginning of this testing protocol, the Display displays the following Screen Instructions:

Shortly, you will see a series of pictures. Press the space bar every time you see a picture except if it is of an animal. Press the spacebar as fast as you can. You are being timed. Remember, press the space bar every time you see a picture except if it is an animal. Press the space bar when you are ready to begin.

The Display then displays pictures of objects, plants, and animals. Each picture is displayed for 2.0 seconds, followed by 1.0 seconds of blank screen. The patient inputs their responses into the Response Input, and thus into the Memory, for further processing by the patient response analysis software. we prefer to use about sixty five stimuli over about 3.3 minutes.

Memory Cabinet Learning

At the beginning of this testing protocol, the Display displays the following Screen Instructions:

In a moment, you will see a cabinet with nine common objects placed on different shelves. You will have twenty seconds to memorize where each object is stored. Study hard. Doors will then close to cover the objects and you will be asked to find them, one at a time. You can do this by either (A) pressing the number key (1–9) on your keyboard that is the same as the door where you think the object is hidden, or (B) pointing and clicking your computer's mouse on the door where you think the object is hidden. If you make a mistake, then the test will remind you where the object is, so that you can find it later. You will be asked to find each object a total of four times. Press the space bar when you are ready to begin.

The user must memorize the locations of nine common objects. In one version, we prefer to use toys as objects. The locations are randomly generated for each user, to minimize users being able to "memorize" the locations. The user is queried about the locations one at a time. The patient inputs their response into the Response Input, and thus into the Memory, for further processing by the patient response analysis software. After one round (9 queries), there is a second 10 second display, and then the process repeats. This continues until the user has been asked for a location of each object four times. If the user guesses incorrectly, then the correct location is briefly shown. If he guesses correctly, the Display displays "correct." Statistics are collected for each round. There is no time limit.

Memory Cabinet Delayed Recall

At the beginning of this testing protocol, the Display displays the following Screen Instructions:

A few moments ago, you saw a cabinet with nine objects placed on different shelves. In a moment, you will be asked to find those items one at a time, just like you did before. This time, you will not see the objects first, and you will not be told if you are right or wrong. Press the spacebar when you are ready to begin.

There is no initial display of objects. The user must recall their locations from Memory Cabinet Learning. The patient inputs their responses into the Response Input, and thus into the Memory, for further processing by the patient response analysis software. There is only one round of queries, and no feedback about the correctness of a response. This test must be given after Memory Cabinet Learning, and preferably after another intervening task.

Scanning Speed and Accuracy

At the beginning of this testing protocol, the Display displays the following Screen Instructions:

Now, look at the sample shapes below. The shapes are in two groups. If both the shapes on the left hand side of the line are also on the right hand side of the line, press the space bar ONCE. If the shapes are not BOTH on the right hand side, then press the space bar TWICE. You only get one chance for each item. Remember—press ONCE for yes and TWICE for no. Work as fast as you can without making any mistakes. Press the space bar when you are ready to begin.

The Display then displays to the patient two groupings of symbols, one on the left side of the Display and one grouping on the right side of the Display, like this:

¿ Ã § ¶ š ? § ¿ Ã Å

Each of approximately thirty groupings of symbols appears separately. The patient inputs their responses into the Response Input, and thus into the Memory, for further processing by the patient response analysis software. We prefer to fix the time required at ninety seconds.

An alternate version of this testing protocol is to ask the patient to hit the number "1" key if one target shape is present on the right side of the Display. and the number "2" key if both target shapes are present there.

Reaction Time

At the beginning of this testing protocol, the Display displays the following Screen Instructions:

Look at the sample white circle below. Each time that you see the white circle, press the space bar. Try and be quick without making mistakes. Press the space bar when you are ready.

The Display then displays a series of pictures to the patient, using a ratio of 1 "target" image (in this example, a white circle) for every several non-target images (in this example, nonwhite circles) displayed.

The patient inputs their responses into the Response Input, and thus into the Memory, for further processing by the patient response analysis software. In our preferred version, in the Reaction Time testing protocol, the visual stimulus duration is 1.5 seconds, followed by 0.5 seconds of blank screen. The patient's response can therefore occur any time within the 1.5 second stimulus, but is not allowed thereafter.

For the personal computer versions of our inventions (in contrast to, for example, the PALM PILOT (TM) based versions), we prefer using certain software operating systems most able to accommodate the rapid response time limits of this testing protocol. Personal computer timers operate independently of the microprocessor speed. Thus, using a 266 MHz microprocessor, or a 450 MHz one, does not affect timer speed. However, different operating systems have different rates of updating the timer. Thus, on WINDOWS 3.11 (TM), WINDOWS 95(TM) and WINDOWS 98(TM) (each commercially available from Microsoft Corp., Redmond, Wash.), the timer is updated only 18.2 times per second, resulting in a maximum resolution of ±27 milliseconds. For many testing protocols, this will have no significant impact.

Cued Reaction Time

At the beginning of this testing protocol, the Display displays the following Screen Instructions:

Press the space bar only-when the white circle is displayed after a black square is displayed. Do not press the space bar if the white circle is displayed after any other shape, nor any other color of square. Remember, press the space bar only when the white circles is displayed after a black square. Try and be quick without making mistakes. Press the space bar when you are ready to start.

The Display then displays the black square followed by white circle pair, in a ratio of 1:6 with total other stimuli. The ratio of the target (white circle) with target primer (black square), to target without a target primer, is 2:1. The patient inputs their responses into the Response Input, and thus into the Memory, for further processing by the patient response analysis software. This portion of the testing protocol takes 3 minutes.

Visual Memory Part I

At the beginning of this testing protocol, the Display displays the following Screen Instructions:

Now, you will see a series of pictures appear on the display. Sometimes, you will see a picture a second time. Each time you see a picture for the second time, press the space bar. Press the space bar when you are ready to begin.

The Display then displays a series of pictures, as for example:

♣ ⌐ ⊗ ♣  ♦ Ø ● ≈ ● ≈

Each of the single forty pictures is displayed for two seconds. Of the forty pictures, twenty are repeated and twenty are not, for a test time of two minutes. The patient inputs their responses into the Response Input, and thus into the Memory, for further processing by the patient response analysis software.

Number Sequencing

At the beginning of this testing protocol, the Display displays the following Screen Instructions:

Below is a key that pairs the numbers 1 through 9 with symbols. Beneath the key, you will see a series of symbols with empty boxes underneath. Fill in the correct numbers for each symbol using the numeric keypad. If you make a mistake, just keep going. Try and fill in as many numbers as you can. Press the space bar once to begin.

The Display then displays, for ninety seconds, a screen like this:

KEY

| β | ø | Þ | ‡ | ‰ | << |
|---|---|---|---|---|---|
| 1 | 2 | 3 | 4 | 5 | 6 |

TEST

| ø | ‰ | ø | << | Þ | ‡ |
|---|---|---|---|---|---|
|   |   |   |   |   |   |
| Þ | ø | ‰ | ‡ | ‰ | ø |
|   |   |   |   |   |   |

The patient inputs their responses into the Response Input, and thus into the Memory, for further processing by the patient response analysis software. In our preferred embodiment, we use animal silhouettes rather than typographic symbols, but words, numbers, and any other visual indicia are all acceptable.

Visual Memory Part II

At the beginning of this testing protocol, the Display displays the following Screen Instructions:

Just a few moments ago, you saw a list of pictures. Some you saw once, others twice. Press the space bar when you see a picture that you recognize from before. It can be one that you just saw once, or one that you saw twice. Press the space bar when you are ready to begin.

The Display then displays a series of pictures, one every two seconds. All the forty pictures from the Visual Memory Part II testing protocol are displayed, in addition to twenty new pictures, over a two minute total time. The patient inputs their responses into the Response Input, and thus into the Memory, for further processing by the patient response analysis software.

Number Recall

At the beginning of this testing protocol, the Display displays the following Screen Instructions:

Now, you will see a series of numbers appear on the display, followed by a display screen with some blanks on it. Using the number keys, enter the numbers in the blanks in exactly the same order as you see them. You can use the backspace key to change your answer if you think you have made a mistake. Press the space bar when you are ready to begin.

The Display then displays a series of individual numerals, one numeral at a time, like this:

5 3

Each group of numerals is displayed for 750 milliseconds. The first groups displayed consist of only two numerals. Latter groups consist of longer and longer groups of numerals:

7 4 8 2 9

The patient inputs their responses into the Response Input, and thus into the Memory, for further processing by the patient response analysis software. The testing protocol continues until the patient makes two consecutive errors on the same level of difficulty (i.e., two consecutive errors with numeral groups having the same quantity of numerals in them). When the patient makes these two consecutive errors, the testing protocol stops. Number sequencing At the beginning of this testing protocol, the Display displays the following Screen Instructions:

Now, you will see a group of numerals appear on the display, followed by a display screen with some blanks on it. Using the numeric keypad, enter the numbers in the blanks in ASCENDING order. That is, order them from lowest to highest. You can use the backspace key to change your answer if you think you have made a mistake. Press the space bar when you are ready to begin.

The Display then displays a group of numbers, like this:

5 3 4

The patient inputs their response (the correct response would be "3 4 5" in the immediate example) into the Memory. Each group of numbers is presented for two seconds. The first groups displayed consist of only three numerals. Latter groups consist of longer and longer groups of numerals:

2 8 3 1 9

The patient inputs their responses into the Response Input, and thus into the Memory, for further processing by the patient response analysis software. The testing protocol is discontinued when the patient makes two consecutive errors on the same level of difficulty (i.e., with two consecutive number groups having the same quantity of numbers in them). This test portion takes approximately three minutes.

Summary

On completion of the testing protocol(s), the patient is informed that the testing is complete. Either after completion of all protocols, or during the test process, the patient's response data is used as variable inputs in the patient response analysis software.

Patient Response Analysis Software

The user's results for the cognitive dysfunction testing protocols are then analyzed statistically, to obtain the most information from them. In our invention, the statistical analysis capability is integrated into the system. This is done by incorporating directly into our system, patient response analysis software. The patient response analysis software uses as variable inputs the testing protocol results discussed above. The patient response analysis software then statistically analyzes these responses and calculates certain values for each specific testing protocol, the values for certain protocols combined, and the values for all the protocols combined. We discuss each in turn.

In our preferred version, we use the following statistical analysis protocols. This compilation of these statistical protocols is protected by copyright, ©2000 PanMedix, Inc.

Individual Testing Protocols

For each separate cognitive dysfunction testing protocol, the patient response analysis software calculates:

t=Average Response Time y=correct responses

O=Errors of Omission (misses or errors)

C=Errors of Commission (false positives, if applicable)

From these, the following ratios can be derived:

Proficiency Index=(O+C)/t

Discriminability=100×[1−(O+C/Number of Stimuli)]

Note that in our preferred embodiment, neither Proficiency Index nor Discriminability are used.

Response Bias=(C−O)/(C+O); if no errors then=0.

Response Variability=mean standard deviation of response times.

Response Variability is calculated for the continuous performance test protocol(s) (e.g., the "Go No-Go Test" above) only.

O Level=y−C−O

Retention Index=100×Delayed Recall/Immediate Recall.

Retention Index is calculated for the memory tests only.

Test—Retest Correlation

If baseline data is available (either from a patient pool, or specifically from a prior test administered to that patient), then the patient response analysis software can also calculate, for each of the above values, the correlation between a given baseline test value ("a") and the value obtained in a subsequent test ("b"). We denote this correlation here as "r(ab)."

$r(ab)=S(ab)/\text{sqrt}[S(aa) \times S(bb)]$

S=Sigma=standard deviation

Mu=mean $S(aa)=\text{SUM}[(a-\text{mean}(a))^2]$ $S(bb)=\text{SUM}[(b-\text{mean}(b))^2]$ $S(ab)=\text{SUM}[abs[(a-\text{mean}(a)) \times (b-\text{mean}(b))]]$ Selectively Combined Testing Protocol Analysis In addition to analyzing data for each testing protocol separately, the patient response analysis software combines the results of certain testing protocols for certain analyses.

General Attention=total correct responses for Number sequencing and Number recall protocols.

Attention Consistency=the weighted number of digits in Number sequencing and Number recall.

Attention Accuracy=(Discriminability for Response Speed+Discriminability for Response Cueing and Inhibition)/2.

Attention Efficiency=(Proficiency for Response Speed+Proficiency for Response Cueing and Inhibition)/2.

Processing Speed Accuracy=(Q Level for Symbol Scanning+Q Level for Number sequencing)/2.

Processing Speed Efficiency=(Proficiency for Symbol Scanning+Proficiency for Number sequencing)/2.

Memory Accuracy=(y for Visual Memory Part I+y for Visual Memory Part II)/2.

Memory Efficiency=(Proficiency for Visual Memory Part I+Proficiency for Visual Memory Part II)/2.

Reaction Time Index=average reaction time for Response Speed+average reaction time for Response Cueing and Inhibition. Processing Speed Index=average reaction time for Symbol Scanning+average reaction time for Number sequencing.

Complex Reaction Time=average reaction time for Visual Memory Part II+average reaction time for Response Cueing and Inhibition.

Total Combined Testing Protocol Values

For all cognitive dysfunction testing protocols combined, the patient response analysis software calculates:

Overall Speed

Overall Accuracy

Overall Proficiency=Overall Speed/Overall Accuracy

In our preferred embodiment, the speed, accuracy and efficiency result indices are generated at the domain level; that is to say, if one cognitive dysfunction testing protocol at baseline is outside the normal range, the software can still generate a statistically meaningful score. If this is not done, then if a patient does not understand the instructions, or has attention deficit disorder, or is disturbed by a telephone call during the test, then that patient's erroneous results will create systematic error which can distort the general score.

Reliable Change Index

The patient response analysis software then calculates a "reliable change index." The reliable change index describes the change from the baseline value, which change is statistically reliable. There are many ways known in the art of statistics to calculate reliable changes. We prefer to calculate the reliable change index (or "RCI") as follows:

$$RCI=X(b)-X(a)/s(d)$$

X(a)=the baseline value

X(b)=the immediate value s(d)=the standard difference for the sub test calculation, as calculated above.

p=the probability of error Regardless of the specific statistical method used to calculate the RCI, the RCI threshold values should, optimally, be set considering generally accepted statistical principles. One tailed and other tests are possible. In our preferred version, the positive and negative RCI threshold values are derived from accepted medical neurology standards. Examples are given in Hinton-Bayre, A. D., "Concussion in Contact Sports: Reliable Change Indices of Impairment and Recovery," *Journal of Clinical and Experimental Neuropsychology*, v. 21, pp. 70–86 (1999). Other values may, however, be used.

For a one tailed test, we prefer to use a negative RCI threshold value of −1.65, with p<0.05. We similarly prefer to use a positive RCI threshold value of −1.04 with p<0.15. Using these amounts, a test result with an RCI<−1.65, indicates symptoms of cognitive dysfunction likely exist in the patient. By contrast, an RCI≧−1.04 indicates symptoms of cognitive dysfunction likely do not exist in the patient. Other threshold values may, of course, be used.

If an RCI value falls outside its negative RCI threshold range, or if there is at least one active cognitive dysfunction symptom in the pre-testing protocol user survey, then the user response analysis software indicates that symptoms of cognitive dysfunction likely exist in the user. Conversely, if all RCI values are within the positive RCI threshold ranges and if there is no active trauma symptom, then the user response analysis software indicates that symptoms of cognitive dysfunction likely do not exist in time user. If at least one RCI value falls inside the negative RCI threshold range but outside the positive RCI threshold range, and if there is no active trauma symptom, then the user response analysis software indicates that symptoms of cognitive dysfunction may exist in the user.

For certain applications (clinical trials, for example), patients can establish a "baseline" score and use this baseline to compare to later scores. In such a use, RCI scores which fall too far outside the normal range (we prefer less than two standard deviations from the mean) are rejected, as cognitive impairment, even severe, may not statistically lower a score which is already quite low. Thus, we prefer to not have such users (nor their physicians) rely on these scores. Low baseline scores could be due to a number of factors including a history of learning problems, distraction and confusion over the instructions, and a conscious attempt to fake a lowered score, in order to manipulate future results.

SUMMARY

Although the present invention has been described in considerable detail with reference to certain preferred versions, other versions are possible. Therefore, the spirit and scope of the appended claims should not be limited to only the description of our preferred versions contained in the foregoing discussion. The features disclosed in this specification, and the accompanying claims and abstract, may be replaced by alternative features serving the same equivalent or similar purpose, unless expressly stated otherwise. Thus, unless expressly stated otherwise, each feature disclosed is one example only of a generic series of equivalent or similar features.

As used in the claims appended, the word "a" includes the singular as well as the plural. The phrase "in communication with" entails both direct communication and indirect communication via one or more intermediary pieces (e.g., microprocessors, cables, etc . . . ).

I claim:

1. A method of measuring the cognitive performance of an individual comprising:
   a. the individual completing at least one cognitive test with at least one testing protocol;
   b. storing result of said at least one cognitive test in a computer readable media; and
   c. applying a reliable change technique to calculate a reliable change measure, wherein the reliable change measure is a statistically meaningful inference of a neurological pathology, wherein the reliable change technique uses at least one baseline of the individual.

2. The method of claim 1, wherein the method is used to quantify the cognitive impairment associated with motion sickness.

3. The method of claim 1, wherein the method is used to quantify the cognitive impairment associated with an insult selected from the group consisting of near drowning, decompression sickness, Caisson Disease, gas embolism, high-altitude sickness, acute mountain sickness, high altitude pulmonary edema, high altitude cerebral edema, Soroche, Puna, and maroe.

4. The method of claim 1, wherein the method is used to quantify the cognitive impairment associated with non-drug medical therapy.

5. The method of claim 4, wherein said non-drug medical therapy comprises ultra-sound treatment.

6. The method of claim 4, wherein said non-drug medical therapy comprises electro-convulsion therapy.

7. The method of claim 4, wherein said non-drug medical therapy comprises radiation therapy.

8. The method of claim 4, wherein said non-drug medical therapy comprises tissue transplant.

9. The method of claim 8, wherein said tissue comprises stem cells.

10. The method of claim 8, wherein said tissue comprises at least part of an anatomical organ.

11. The method of claim 8, wherein said tissue comprises fetal tissue.

12. The method of claim 8, wherein said tissue consists essentially of genetic material.

13. The method of claim 4, wherein said non-drug medical therapy comprises nuclear medicine.

14. The method of claim 1, wherein the method is used to quantify the cognitive impairment associated with excessive exposure to radiation.

15. The method of claim 14, wherein said radiation comprises electric shock.

16. The method of claim 14, wherein said radiation comprises sunlight.

17. The method of claim 14, wherein said radiation comprises ambient electromagnetic radiation due to an electromagnetic device.

18. The method of claim 1, wherein said neurological pathology is related to a focal brain disorder of a higher function.

19. The method of claim 18, wherein said focal brain disorder of a higher function is amnesia.

20. The method of claim 18, wherein said neurological pathology is a supratentorial or subtentorial mass lesion.

21. The method of claim 1, wherein said neurological pathology is a global-diffuse cerebrum disorder.

22. The method of claim 21, wherein said global-diffuse cerebrum disorder is caused by mechanical trauma.

23. The method of claim 21, wherein said global-diffuse cerebrum disorder is anoxia or ischemia.

24. The method of claim 21, wherein said global-diffuse cerebrum disorder is selected from the group consisting of: epilepsy, postictal states and psychomotor status epilepticus.

25. The method of claim 21, wherein said global-diffuse cerebrum disorder is a subarachnoid hemorrhage.

26. The method of claim 21, wherein said global-diffuse cerebrum disorder is caused by a exogenous or endogenous toxin.

27. The method of claim 21, wherein said global-diffuse cerebrum disorder is dementia.

28. The method of claim 27, wherein said dementia is selected from the group consisting of chronic drug, alcohol or nutritional abuse.

29. The method of claim 27, wherein said dementia is Huntington's disease.

30. The method of claim 27, wherein said dementia is dementia paralytica.

31. The method of claim 27, wherein said dementia is Creutzfeldt-Jacob disease.

32. The method of claim 27, wherein said dementia is selected from the group consisting of Wilson's disease and parkinsonism.

33. The method of claim 27, wherein said dementia is selected from the group consisting of Alzheimer's presenile dementia, Alzheimers senile onset dementia, Pick's disease and simple idiopathic presenile dementia.

34. The method of claim 27, wherein said dementia is associated with severe bead injury.

35. The method of claim 1 wherein said neurological pathology is selected from the group consisting of cerebrovascular disease, multi-infarct dementia and chronic communicating hydrocephalus.

36. The method of claim 1, wherein said neurological pathology is selected from the group consisting of: a demyelinating disease, multiple sclerosis, amytropic lateral sclerosis, a central nervous system infection and a central nervous system neoplasm.

37. The method of claim 1, wherein said neurological pathology comprises attention deficit disorder.

38. The method of claim 1, wherein said method is used to assess changes in said user's condition over time, to determine a proper time to discharge said user from a medical care facility.

* * * * *